(12) United States Patent
Christensen et al.

(10) Patent No.: US 6,653,096 B1
(45) Date of Patent: *Nov. 25, 2003

(54) PROCESS CHALLENGE DEVICE AND METHOD

(75) Inventors: Dennis Christensen, San Jose, CA (US); R. Daniel Webster, Sunnyvale, CA (US); Harvey A. Markinson, Alameda, CA (US)

(73) Assignee: Process Challenge Devices, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/379,682

(22) Filed: Aug. 24, 1999

Related U.S. Application Data

(63) Continuation-in-part of application No. 08/887,753, filed on Jul. 3, 1997, now Pat. No. 5,942,408.
(60) Provisional application No. 60/022,393, filed on Jul. 29, 1996.

(51) Int. Cl.$^7$ .................................. C12Q 1/22
(52) U.S. Cl. .................. 435/31; 435/287.4; 435/287.7; 435/808
(58) Field of Search ................ 435/31, 287.1, 435/287.4, 287.7, 287.8, 805; 422/1, 26, 28, 32, 56, 58

(56) References Cited

U.S. PATENT DOCUMENTS

| | | | | |
|---|---|---|---|---|
| 3,711,378 A | * | 1/1973 | Kereluk | 435/287.4 |
| 4,121,714 A | * | 10/1978 | Daly et al. | 206/363 |
| 4,636,472 A | * | 1/1987 | Bruso | 435/287 |
| 5,759,848 A | * | 6/1998 | Nagoshi et al. | 435/287.1 |
| 5,830,683 A | * | 11/1998 | Hendricks et al. | 435/31 |
| 5,866,356 A | | 2/1999 | Albert et al. | |
| 5,942,408 A | | 8/1999 | Christensen et al. | |

FOREIGN PATENT DOCUMENTS

| | | |
|---|---|---|
| EP | 0 093 920 A1 | 11/1983 |
| EP | 0 152 298 A2 | 8/1985 |
| EP | 0 421 760 A1 | 4/1991 |
| FR | 2 521 906 A1 | 8/1983 |
| GB | 2 186 974 A | 8/1987 |
| WO | WO 96/06184 A1 | 2/1996 |

* cited by examiner

Primary Examiner—David A. Redding
(74) Attorney, Agent, or Firm—Carol D. Titus; Gregory Smith & Associates

(57) ABSTRACT

A process challenge device tailored to mimic the resistance of a particular product-package combination to a particular biological inactivation, disinfection, or sterilization process. The device is used to challenge the process, thus providing a means to validate the efficacy of the process. In one embodiment, the process indicator includes a biological indicator organism stored on a carrier enclosed within a chamber formed by a barrier film material. The specific indicator organism and carrier substrate are chosen for their appropriateness for a given process. The materials comprising the barrier film material of the process challenge device are chosen for the materials' specific resistance to the given process. The process challenge device may also comprise a separate second chamber filled with an appropriate culture medium or enzyme substrate that is separated from the chamber containing the process indicator by a separation means, such as a valve, a clip, or a frangible separation. The separation means between the two chambers is capable of being removed on demand after completion of the process thus allowing the culture medium or enzyme substrate to contact the process indicator.

24 Claims, 3 Drawing Sheets

PROCESS CHALLENGE DEVICE AND METHOD

ROSS REFERENCE TO OTHER APPLICATIONS

This application is a continuation-in-part of U.S. application Ser. No. 8/887,753 filed Jul. 3, 1997, now U.S. Pat. No. 5,942,408 which claims priority of U.S. Provisional Patent Application No. 60/022,393 filed on Jul. 29, 1996, the applications of which are hereby incorporated by reference in their entirety.

FIELD OF THE INVENTION

This invention relates generally to process challenge devices, in particular to process challenge devices using process indicators such as biological indicator organisms or biological enzymes sealed in containers made from specially chosen materials, used to assess the efficacy of procedures for the inactivation of microorganisms in industries related to health care, food packaging and preparation, and other industries that use biological indicators.

BACKGROUND OF THE INVENTION

There are several conventional methods to test the effectiveness of a given sterilization, disinfection, or biological inactivation process (hereafter referred to collectively as "inactivation process"). A first method is to inoculate a sample product with a known quantity of a specific indicator organism (the "inoculate"), subject the inoculated product to the appropriate process, recover the sample inoculate, and culture the inoculate in a specific growth medium to determine whether there were any surviving organisms. A second method is to use a biological indicator which is inoculated with a known quantity of a specific indicator organism, subject the biological indicator to the appropriate process, and culture the biological indicator to determine whether there are any surviving organisms. Typically, in both the first and second methods the absence of growth of the indicator organisms in the growth medium indicates a successful inactivation process. Direct inoculation of sample product is generally done during early validation of a biological inactivation process. Biological indicators are generally used to test repeat processing. A third method is to use an indicator enzyme, subject the enzyme to the appropriate process, and then test for enzyme activity. If no activity is indicated, it is presumed that living organisms would similarly be inactivated.

Currently there are three primary inactivation processes employed in the health care industry: steam, ethylene oxide gas, and ionizing radiation. Several other processes such as dry heat, hydrogen peroxide, chlorine dioxide, peracetic acid, ozone, and plasma are also in various stages of use and acceptance.

Each of these inactivation processes require unique biological indicator organisms, growth media, and procedures to confirm sterilization effectiveness. Among the problems associated with confirming biological inactivation and thus the effectiveness of process are: (a) the lack of commercial availability of appropriate carrier media for some of the newer processes; (b) the difficulty in inoculating products to be tested due to product/package configuration; (c) the cost of using actual products that must be sacrificed for the initial process qualification and the lot-to-lot verification of the process in every process test cycle; and (d) concerns regarding worker exposure to certain of the chemical sterilants, (for example, the European Standard for ethylene oxide processing requires removal of the biological samples prior to degassing the product).

Self-contained process challenge devices containing biological indicator organisms which do not require inoculation of a product are in use in health care facilities such as hospitals. The resistance of a process challenge device to a particular biological inactivation process is given as a D Value which is defined as the exposure time required under a defined set of conditions to cause a 1-logarithm or 90% reduction in the population of a particular organism. Process challenge devices currently on the market have a single unchanging D Value. In order to create the higher resistance to the inactivation process experienced by actual product being processed, due to packaging of the product, the location of a product within a load being processed, or other factors, these devices must generally be wrapped or contained within packaging or other protective material similar to that used on the products being sterilized, so that the process challenge device is exposed to the same environment as the products being processed. Alternatively, in some cases the process challenge device is buried in the most protected location within a load being sterilized. 5 Therefore, these devices cannot be used alone to validate a biological inactivation process without additional protection from the process to simulate the higher resistance of the actual products to the process.

For example, Welsh et al., 4,839,291, discloses a process challenge device that is composed of a number of elements including an outer tube and an inner tube assembled in a manner intended to create a tortuous path to impede the flow of sterilant to the biological indicator contained within the tubes, thereby creating a D Value. Typical of many prior art devices, the device of Welsh et al. is larger and more expensive to manufacture than the present invention, and its resistance to a particular sterilization process may not be easily and accurately varied merely by using slightly different materials in construction of the device. Additionally, the materials used may not be suitable for the newer inactivation processes, such as hydrogen peroxide, ozone, and plasma, because the sterilants used may destructively react with elements of the Welsh et al. process challenge device.

It would be a significant advantage to provide a process challenge device which overcomes the disadvantages of the prior art devices, and that can, in addition, be constructed with resistance tailored to a particular biological inactivation process to avoid the need for destructive testing of product, the need for additional packaging of or protective covering over the process challenge device, or the necessity of placing one or more devices within an actual load. Therefore, what is needed is: (1) a convenient, low cost device to challenge biological inactivation process effectiveness, (2) a process challenge device that may be easily constructed with variable resistance to a particular biological inactivation process by substitution of known materials having known resistances to the particular process, (3) a process challenge device which can be constructed with a resistance to a particular biological inactivation process at least as great as the resistance of the product typically processed, so that the process challenge device may be used alone to test the inactivation process, without accompanying materials or products, (4) a package system containing a biological indicator and, optionally, an integral growth medium that is specific to any given biological inactivation process, (5) a process challenge device that can be safely, conveniently, and easily recovered for subsequent culturing to confirm and assure process effectiveness.

SUMMARY OF THE INVENTION

The present invention is a process challenge device that includes a single or multi-chamber sealed pouch or the like that contains at least one process indicator such as a biological indicator organism, biological enzyme, or other indicator used to determine the efficacy of a biological inactivation process. In embodiments having a second chamber, the second chamber may contain a cell culture medium or enzyme substrate. The pouch is composed of one or more layers of a web or film material (hereafter referred to as "film material"). Different portions of the device may be formed of different materials.

Domestic and international regulatory guidelines permit the use of biological process challenge devices that demonstrably have resistance to sterilization equal to or greater than the material or product and package combination to be subjected to the process being tested by the process challenge device. The product and package combination (hereafter "product-package combination") refers to the characteristics of the product itself and of any associated packaging which may exist as these characteristics relate to or effect the product-package combinations resistance to a particular inactivation process. A product-package combination including no packaging is included in this definition.

The pouch of the present invention is fabricated from a suitable single or multiple film layer or multi-layer film laminate that is chosen to offer the appropriate level of resistance to the inactivation process. The magnitude of resistance to the inactivation process is determined by knowledge of the following factors: (1) the product and packaging configuration and characteristics, (2) the biological inactivation method of choice, and (3) the appropriate laboratory studies confirming the equivalency of biological inactivation of the device to the specific product-package combination. The resistance of the film material is typically measured by gas permeation, and temperature and chemical resistance values, which are well known in the industry.

By knowing the relevant factors, and by referencing the known gas permeation, temperature and chemical resistance values of available film materials, the specific film material or materials to be used in construction of the process challenge device may be chosen. This results in a process challenge device that can be used alone to mimic the resistance to the inactivation process experienced by the product-package combination being processed, rather than requiring that the process challenge device be processed with an actual load, or with additional packaging or protections to simulate resistance of the product-package combination to the process.

Any process indicator capable of being used to measure the efficacy of the inactivation process may be used. Biological indicator organisms are typically available commercially in the form of a carrier media such as small cellulose disks or strip carriers inoculated with a known population of a known organism. However, it is comprehended that other carrier media may be used with the present invention. Such other carrier media may include metals, fiber glass, microporous polymeric compounds including polypropylene, polyethylene, and polysulfone, and ceramics. Biological enzyme indicators are also commercially available. Such enzymes are frequently provided in the form of an enzyme tablet, but they may also be provided on a carrier media.

In some embodiments, the process challenge device of the invention may include process exposure indicators. Any means for visually indicating that the device has been exposed to the inactivation process may be used, however, a paper label that is chemically treated to change color when the device has been exposed to the biological inactivation process is preferable.

The process challenge device of the invention may also contain a separate additional chamber containing a test medium. In embodiments in which the process indicator is a biological indicator organism, the test medium may be a culture medium tailored for the specific biological indicator organism. In embodiments where the process indicator is a biological enzyme, the test medium may be an enzyme substrate chosen for use with the biological enzyme. The second chamber is separated from the first chamber containing the process indicator by a separation means, such as a valve, a clip, heat seal, or a frangible separation. The separation means between the two chambers is capable of being opened, ruptured, or removed on demand after completion of the inactivation process, to allow the culture medium or enzyme substrate, as appropriate, to contact the process indicator. In embodiments using biological indicator organisms, this initiates the beginning of the culture phase, which confirms non-survivability of the organism population and thus process efficacy. In embodiments using biological enzymes, the observation of no enzyme activity indicates that any living organisms would similarly have been inactivated. The incorporation of the culture medium or enzyme substrate into the device permits a level of convenience to the user not available in prior art inventions.

DETAILED DESCRIPTION OF THE INVENTION

Biological inactivation process validation, and verification of process effectiveness, are important aspects of any inactivation process for medical devices or pharmaceuticals or any treatment process for sterilization, biological inactivation, or disinfection of food products.

Conventional means to test the effectiveness of a given inactivation process require the inoculation of sample product with a known quantity of a specific indicator organism (the "inoculate"), subjecting the inoculated product to the appropriate process, recovering the sample inoculate, and culturing the inoculate in an appropriate growth medium to determine whether any indicator organisms survive.

The international guidelines for sterilization of health care products allows for the use of a "process challenge device" as an alternative to the conventional method of process validation, and biological inactivation verification, described above. In methods using a process challenge device, the process challenge device is cycled through the process with the products and then separately analyzed to determine the efficacy of the process. The process challenge device must be as resistant or more resistant, to the inactivation process than the product-package combination being sterilized. Normally this requires that the process challenge device be protected within actual product being processed, or be otherwise protected in order to mimic the resistance of the product to the process.

Figure 1:
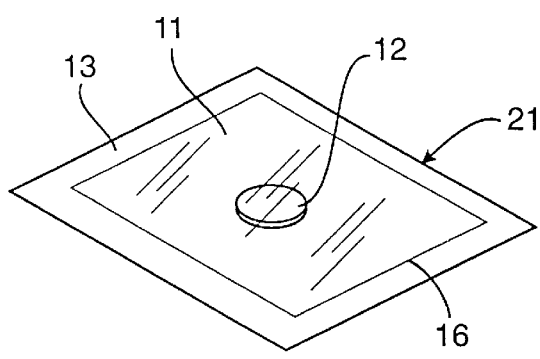
FIG. 1 is a perspective view of a first embodiment of the process challenge device of the present invention wherein the process indicator is a cellulose disk substrate carrying a known population of a biological indicator organism.
Figure 2:
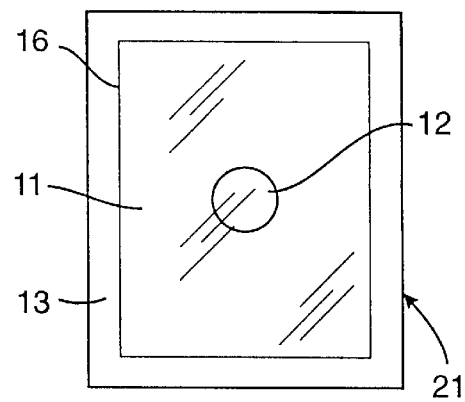
FIG. 2 is a plan view of the process challenge device of FIG. 1.

A first embodiment of the process challenge device of the present invention, is shown in FIGS. 1 and 2, generally referenced by the number 21. In this embodiment, the process challenge device has a chamber 16, enclosed by a barrier film material 11. The chamber 16 of the process challenge device 21 may be formed by sealing two separate pieces of barrier film material 11 together to form a front and a back panel or a single continuous piece of barrier film material 11 may be folded and sealed to form chamber 16. Where two pieces of barrier film material 11 are used, the front and back panels may be made of the same or different material. The barrier film material 11 is sealed by a peripheral seal 13 around the edges of the chamber 16. Within the chamber 16 is a process indicator 12. In the embodiment shown, chamber 16 encloses a cellulose disk inoculated with a known quantity of a biological indicator organism, which may be one of several types and concentrations chosen for the organism's appropriateness to the method of biological inactivation to be used. For example, the recommended concentration of *Bacillus subtilis* for use in ethylene oxide gas sterilization processes is $10^6$ (microorganisms per indicator), typically stored on a cellulose carrier. The international guidelines for steam sterilization recommend a process indicator with a $10^6$ concentration of *Bacillus stearothermophilus*. For food processing a process indicator inoculated with Clostridium is preferred. Other preferred microorganisms include *Bacillus circulans, Bacillus cereus*, and *Bacillus Pumilus*. In still other embodiments, other process indicators, such as a biological enzyme, could be used.

Other newer types of inactivation processes, such as hydrogen peroxide, ozone, plasma, or chlorine dioxide may be reactive with the cellulose carrier typically used to carry a biological indicator. Therefore, for these processes, a carrier other than cellulose should be used in process indicator 12, such as a fibrous polyester carrier, a porous ceramic carrier, fiber glass carrier, or a carrier composed of plastics such as microporous polymeric compounds including polypropylene, polyethylene, or polysulfone, or a nonporous inorganic substrate such as a metal, glass or fiberglass.

Barrier film material 11 of the process challenge device 21 is designed to create a specific resistance greater than or equal to that of the material or product-package combination being treated by a specific process. The process resistance of the challenge device is determined by the properties of the barrier film material or materials chosen. Such properties include gas permeability, radiation transmission, and temperature and chemical resistance. Suitable candidate materials for barrier film material 11 include, but are not limited to, polymer film materials, such as polyolefins (e.g. polyethylene or polypropylene), polyesters (e.g. polyethylene terephthalate (mylar®)), polybutylene terephthalate, PETG copolyester, polyamides (nylons), vinyl-chloride polymers, polyvinylidene chloride (e.g. SARAN®), polyvinylidene fluoride, polyamides, ethylene-vinyl acetate, ethylene vinyl alcohol, aluminized polyester, etc., or nonpolymer films, such as aluminum foil, silica oxide and alumina oxide. These materials may be used either separately or in combination. Multilayer films which are laminated with adhesive or formed by coextrusion may also be used. If desired, barrier film material 11 may also include vent materials, such as spun bonded polyolefin (e.g.

Tyvek® or the like) or expanded polytetrafluoroethylene (e.g. Goretex® or the like). Barrier film material 11 may constitute an inner barrier film material enclosed within an outer barrier film material to simulate the sterilization resistance of double-pouch packaging which is currently prevalent for packaging surgical devices and interventional products. The specific materials and conformation chosen will vary depending on the characteristics of the inactivation process in which the process challenge device 21 will be used.

Process indicator 12 is placed within chamber 16. Chamber 16 is then sealed by a peripheral seal 13 around the edges of barrier film material 11. The method of making the peripheral seal 13 around the edges of barrier film material 11 is chosen (a) for compatibility with the material or materials of barrier film material 11, and (b) to provide an appropriate level of process resistance. Methods for making peripheral seal 13 include but are not limited to heat sealing, including isothermal, impulse and radio frequency heating, ultrasonic sealing and adhesive sealing. The interior of chamber 16 within barrier film material 11 may be filled with a selected atmosphere, such as sterile air, filtered air, or an inert gas. Alternatively, barrier film material 11 may be vacuum sealed after biological indicator 12 is placed within chamber 16.

The exterior appearance of the process challenge device 21 may be in the format of a flexible heat-sealed pouch, as illustrated in FIGS. 1 and 2. However, in alternative embodiments, the process challenge device may be made in other formats such as a heat-sealed thermoformed tray or a form-fill-and-seal pouch or tray. The choice of the format and the manufacturing process for the process challenge device will depend on, among other things, the material or materials selected for barrier film material 11, the nature of the product-package combination, the particular process in which the process challenge device will be used, and the economics of the process challenge device manufacturing process.

In some embodiments, process challenge device 21 may include one or more process exposure indicators. Any means appropriate for visually indicating that the device has been exposed to the inactivation process may be used, and a large number and variety of such indicators are commercially available, however, a paper label that is chemically treated to change color when the device has been exposed to the biological inactivation process is preferable.

In use, for either process validation or process verification, a process challenge device 21, constructed with materials chosen to mimic the resistance of a specific product-package combination to the inactivation process, is used. Alternatively, one or more process challenge devices 21 are placed at various locations within a load or processing batch, preferably on the exterior of the product packaging at different locations within the load. Time is saved by not having to inoculate sample products before they are packaged and no actual packaged products have to be sacrificed. The load is then subjected to the chosen sterilization or inactivation cycle or other applicable process. After the process cycle, the process challenge devices 21 are removed and taken to a laboratory for analysis to determine the efficacy of the inactivation process. In embodiments using a biological indicator organism for process indicator 12, the process indicator is removed from chamber 16 and incubated in an appropriate culture medium for culturing. The absence of growth of indicator organisms indicates a successful sterilization, biological inactivation process, or disinfection process. In embodiments using biological enzyme indicators, the process indicator is removed and exposed to an appropriate enzyme substrate to determine whether any enzyme activity remains.

Significant time is saved, and personnel exposure to any residual sterilizing agent in the sterilized products is reduced, because the packages do not have to be opened for retrieval of the process challenge devices. A reduction in exposure to residual sterilizing agent is an important advantage of the invention over the prior art for ethylene oxide gas sterilization because ethylene oxide gas is a suspected carcinogen and under current regulations employee exposure to the residual gas must be limited to 0.5 PPM/8 hours.

Figure 3:
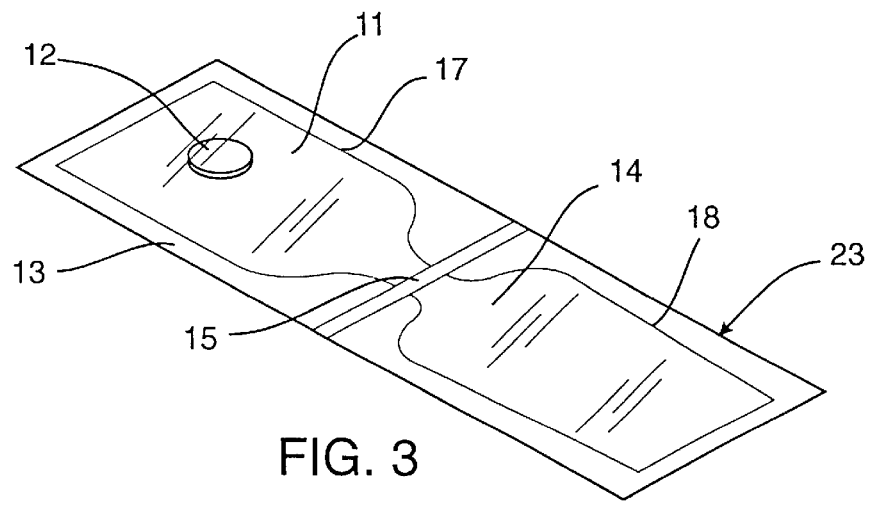
FIG. 3 is a perspective view of a second embodiment of the process challenge device having an integral culture medium chamber.
Figure 4:
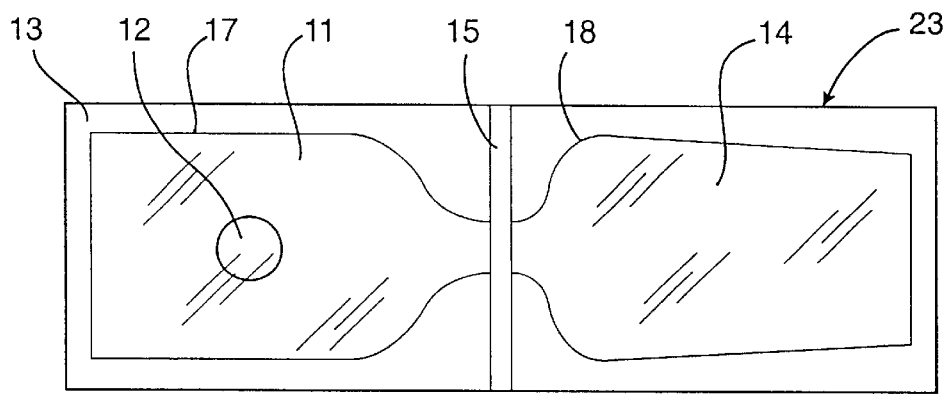
FIG. 4 is a plan view of the process challenge device of FIG. 3.

A second embodiment of the process challenge device of the present invention, generally referenced by the number 23, is shown in a perspective view in FIG. 3 and in a plan view in FIG. 4. In this second preferred embodiment, the process challenge device 23 has a first chamber 17 and a second chamber 18 enclosed within a barrier film material 11. The process challenge device 23 may be formed by sealing two separate pieces of barrier film material 11, formed of either the same or different material, together to form a front and a back panel or by folding and sealing a single continuous piece of barrier film material 11. In alternate embodiments, a different barrier film material may be used for each chamber. The barrier film material 11 is sealed by a peripheral seal 13 around the exterior edges of the first chamber 17 and the second chamber 18. The first chamber 17 and the second chamber 18 are physically separated by a breachable separation means such as a frangible seal 15. Alternative separation means may include clips or valves or other known separation means, preferred embodiments of which can be seen in FIGS. 5 and 6, in which a process indicator 12 is enclosed within the first chamber 17.

Second chamber 18 may be filled with a test medium that is caused to pass through frangible seal 15 to contact process indicator 12 to begin the process of analyzing the effectiveness of the inactivation process to which the process challenge device 23 was subjected. For example, in embodiments using a process indicator comprising a biological indicator organism, the test medium is preferably an appropriate culture medium 14, which may be one of several types chosen for its appropriateness to the indicator organism used and the method of biological inactivation to be used. A liquid culture medium such as a soybean casine digest medium or the like is preferred for culture medium 14. In alternative embodiments, a gelatin medium could be used. In embodiments using a process indicator comprising a biological enzyme, the test medium may be an appropriate enzyme substrate.

Other newer types of inactivation processes, such as hydrogen peroxide or ozone plasma may be reactive with the cellulose carrier typically used to carry biological organisms. Therefore, for these processes, a carrier other than cellulose should be used for process indicator 12, such as a fibrous polyester substrate, a porous ceramic, fiber glass, or a substrate composed of plastics such as microporous polymeric compounds including polypropylene, polyethylene, and polysulfone, or a nonporous inorganic substrate such as a metal, glass or fiberglass. For example, in a process challenge device embodiment for hydrogen peroxide sterilization, the process indicator 12 preferably has a $10^6$ concentration of *Bacillus stearothermophilus* on a non-reactive carrier comprising a microporous filter medium, preferably of a non-reactive polymer such as polypropylene, polyethylene or polysulfone. In alternate embodiments, other desirable microorganisms may be used.

The barrier film material 11 surrounding first chamber 17, which contains process indicator 12, is chosen to be as resistant or more resistant to the inactivation process than the product-package combination to be treated. Barrier film material 11 surrounding second chamber 18, may be identical to barrier film material 11 of first chamber 17, or a different barrier material may be chosen. For example, in an embodiment using a biological indicator organism, the second chamber 17 would preferably contain a culture medium. Depending on the culture medium 14 and the inactivation process chosen, a more resistant barrier material may be preferred for second chamber 18 in order to protect culture medium 14 from the biological inactivation process. If for example, the chosen culture medium 14 is reactive to the sterilizing agent used in gas sterilization, a gas impermeable barrier material may be used for barrier film material 11 of second chamber 18. Similarly, if the chosen culture medium 14 is susceptible to radiation degradation, then a barrier material that is more opaque to the wavelength or the particle energy used for radiation sterilization may be used for barrier film material 11 of second chamber 18. Alternatively, in some circumstances it may be desirable to use a less resistant barrier material for barrier film material 11 of second chamber 18 if it is desired to assure the sterility of culture medium 14 simultaneously with sterilizing the materials to be treated.

Suitable candidate materials for barrier film material 11 include, but are not limited to, polymer film materials, such as polyolefins (e.g. polyethylene or polypropylene), polyesters (e.g. polyethylene terephthalate (MYLAR®), polybutylene terephthalate, PETG copolyester, polyamides (nylons), vinyl-chloride polymers, polyvinylidene chloride (e.g. SARAN®), polyvinylidene fluoride, polyamides, ethylene-vinyl acetate, ethylene vinyl alcohol, aluminized polyester, etc., or nonpolymer films, such as aluminum foil, silica oxide and alumina oxide. These materials may be used either separately or in combination. Multilayer films which are laminated with adhesive or formed by coextrusion may also be used. If desired, barrier film material 11 may also include vent materials, such as spun bonded polyolefin (e.g. Tyvek® or the like) or expanded polytetrafluoroethylene (e.g. Gore-Tex® or the like). Barrier film material 11 may constitute an inner barrier film material enclosed within an outer barrier film material to simulate the sterilization resistance of double-pouch packaging which is currently prevalent for packaging surgical devices and interventional products. The specific materials and conformation chosen will vary depending on the characteristics of the inactivation process in which the process challenge device 23 will be used.

Peripheral seal 13 around the edges of barrier film material 11 may be made by any acceptable means including, but not limited to, ultrasonic sealing, adhesive sealing, or heat sealing by isothermal, impulse or radio frequency heating. If desired the interior of first chamber 17 and/or second chamber 18 may be filled with a selected atmosphere.

In some embodiments, the process challenge device 23 of the present invention may include process exposure indicators. Any means for visually indicating that the device has been exposed to the inactivation process may be used, however, a paper label that is chemically treated to change color when the device has been exposed to the biological inactivation process is preferable. A variety of such exposure indicators are commercially available.

In the embodiment seen in FIGS. 3 and 4, the frangible seal 15 which separates first chamber 17 and second chamber 18 may also be made by heat sealing, including isothermal, impulse and radio frequency heating, ultrasonic sealing or adhesive sealing. Frangible seal 15 is preferably more susceptible to rupture than peripheral seal 13. This may be done by using a weaker adhesive, or a lower heat sealing temperature for sealing frangible seal 15 than is used on the peripheral seal 13. The geometry of frangible seal 15 may also be used to enhance the ease of rupturing frangible seal 15 relative to peripheral seal 13. For example, frangible seal 15 may have a seal width that is narrower than that of peripheral seal 13. Alternatively, a stress riser, like the chevron shaped seal or a narrow passage 22, as shown in FIGS. 3, 4, and 7, connecting first chamber 17 and second chamber 18 may be used to concentrate the pressure, thus making the frangible seal 15 more easily ruptured.

Figure 5:
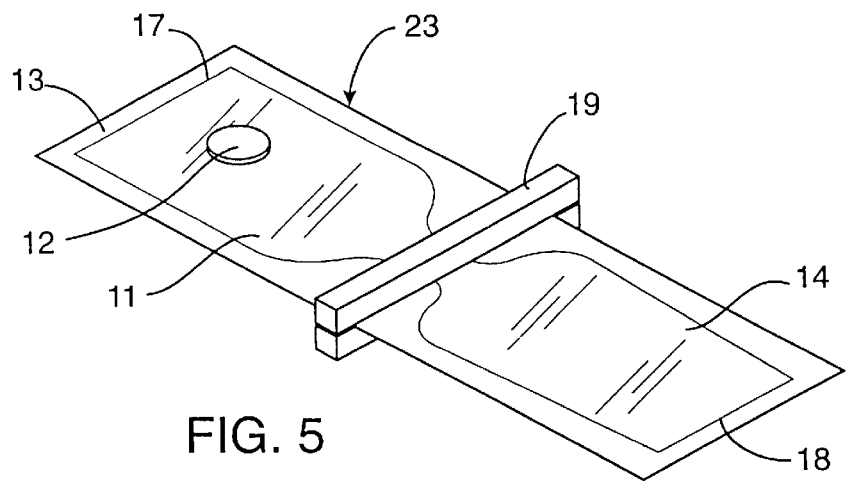
FIG. 5 is a plan view of the second embodiment of the process challenge device of FIG. 4 having a clip separating the process indicator chamber from the culture chamber.

In an alternative embodiments seen in FIG. 5, a clip 19 may be used to separate first chamber 17 and the second chamber 18 until it is desired that the contents of each chamber come into contact. For example, in an embodiment using a biological indicator organism, after the process challenge device 23 has been subjected to the appropriate process, the clip is simply removed and the culture medium 14 is caused to contact the process indicator 12. Any clip that will effectively prevent culture medium 14 from entering first chamber 17 until the clip is removed may be used.

Figure 6:
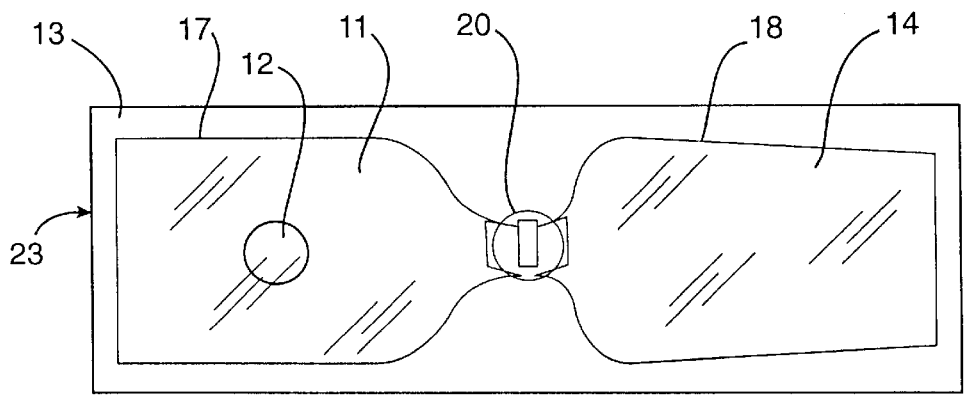
FIG. 6 is a plan view of the second embodiment of the process challenge device of FIG. 4 having a valve separating the process indicator chamber from the culture chamber.

In other embodiments such as FIG. 6, a valve 20 may be used to separate first chamber 17 and second chamber 18. In this embodiment, after process challenge device 23 has been subjected to the appropriate process, valve 20 is opened and culture medium 14 is then caused to contact the biological indicator 12. Any valve that will effectively prevent culture medium 14 from entering first chamber 17 until valve 20 is opened may be used.

Figure 7:
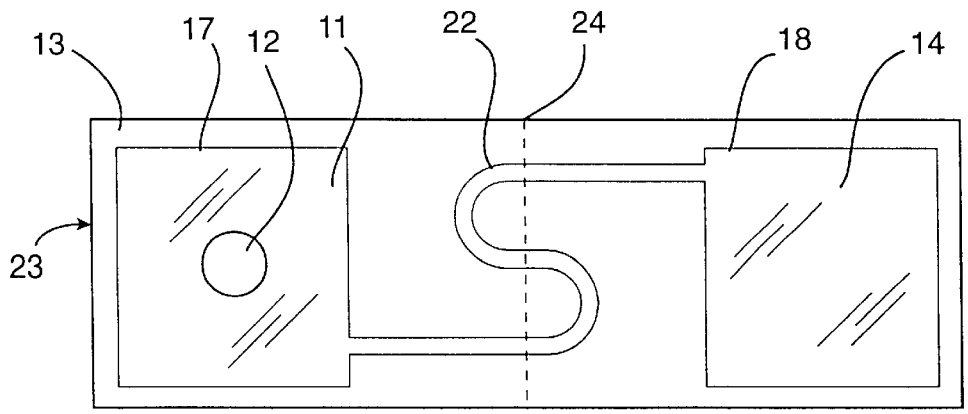
FIG. 7 is a plan view of the third embodiment of the process challenge device of FIG. 4 having a tortuous path separating the process indicator chamber from the culture chamber.

In a third preferred embodiment, best seen in FIG. 7, a tortuous path 22 is used to separate first chamber 17 from second chamber 18. Resistance to the passage of medium 14 from second chamber 18 to first chamber 17 can be adjusted by varying the geometry of the channel of tortuous path 22. Reference number 24 points to a dotted line which is intended to indicate a fold line. Folding the process challenge device 23 along fold line 24 provides an additional barrier to the passage of medium 14 from second chamber 18 to first chamber 17. In alternate embodiments, only tortuous path 22 or only fold line 24 could be used to prevent passage of medium 14 from one chamber to the other, rather than both tortuous path 22 and fold line 24 as shown.

Figure 8:
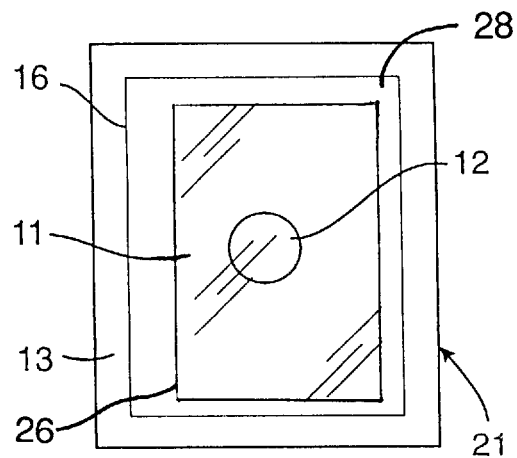
FIG. 8 is a plan view of the fourth embodiment of the process challenge device having a window into the chamber.

The fourth embodiment, shown in FIG. 8, has a window or vent 26 leading into the chamber 16. The window 26 is made of the barrier material 11. The size, location and material of the window 26 should be chosen to mimic the resistance of the material or product packaging. The remaining portion of the chamber 16 is formed of any other suitable chamber material 28 with an equal or greater resistance than the barrier material 11. In this embodiment, the chamber material 28 may be opaque, translucent or transparent. In cases where the barrier material 11 is expensive or difficult to work with, manufacturing costs may be reduced by using a chamber 16 with a window 26 of the barrier material 11.

Figure 9:
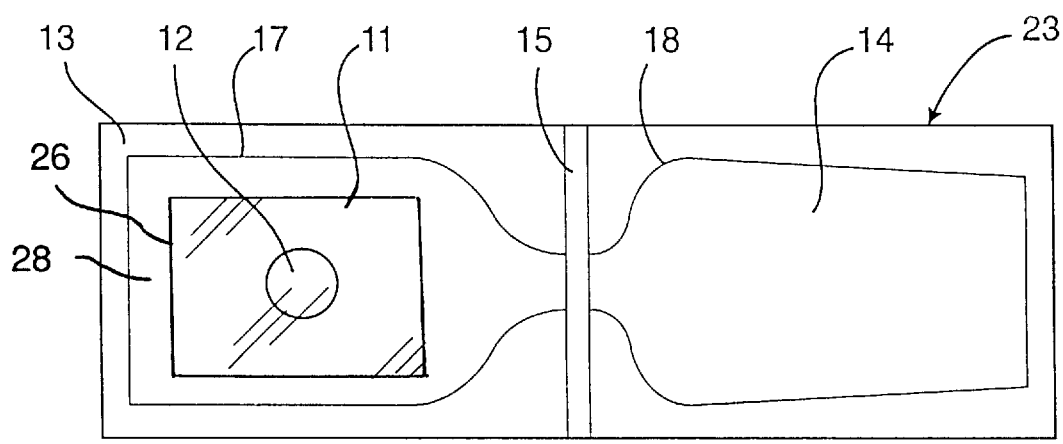
FIG. 9 is a plan view of the fifth embodiment of the process challenge device having a window into the indicator chamber.

The fifth embodiment, shown in FIG. 9, has a window 26 into the first or indicator chamber 17. The window 26 is again made of the barrier material 11. The size, location and material of the window 26 should be chosen to mimic the resistance of the material or product packaging. The remaining portion of the chamber 17 and the second chamber 18 are formed or any other suitable chamber material 28 with an equal or greater resistance than the barrier material 11. The chamber material 28 may be opaque, translucent or transparent.

In use, for either process validation or process verification, a process challenge device 23 is preferably constructed with materials chosen to mimic the resistance of an actual product-package combination exposed to the inactivation process. One or more process challenge devices 23 are preferably placed at various locations within a load or processing batch. If multiple process challenge devices 23 are used, it is preferable to place the process challenge devices 23 on the exterior of the product packaging and at different locations within the load. The load is then subjected to the chosen biological inactivation cycle or other applicable process. After the process cycle, the process challenge devices 23 are removed from the load and the separation means between first chamber 17 and second chamber 18 is broken or removed, allowing transfer of the culture medium 14 to the first chamber 17 containing the process indicator 12. There is no need to transfer the process challenge device 23 to a laboratory, as everything needed for culturing the indicator organism or testing for enzyme activity is contained within the process challenge device 23. For example, process challenge devices using a biological indicator organism require only an incubator or other controlled temperature chamber is to incubate the process indicator 12 in the culture medium 14. The absence of growth of the indicator organisms indicates a successful sterilization, biological inactivation process or disinfection process.

Significant savings are realized by using the two chamber embodiment of the process challenge device 23 because further time and expense are saved because minimal laboratory facilities and personnel are required to analyze the results of each process challenge device 23. For example, in embodiments using biological indicator organisms, time is saved in not having to prepare culture medium or culture tubes in which to incubate the indicator organisms, thereby avoiding the need for a complete laboratory. By eliminating many of the laboratory procedures, the level of training needed for most of the process steps of inactivation process validation or process verification are also reduced. Exposure of personnel to the indicator organisms and to any residual sterilizing agent is also reduced.

The preferred embodiments described herein are illustrative only and although the examples given include many specificities, they are intended as illustrative of several possible embodiments of the invention. Other embodiments and modifications will, no doubt, occur to those skilled in the art. For example, any process indicator may be used within the chambers of the present invention. Thus, the examples given should only be interpreted as illustrations of some of the preferred embodiments of the invention, and the full scope of the invention should be determined by the appended claims and their legal equivalents.

What is claimed is:

1. A process challenge device comprising:
a first chamber formed by a first barrier film; and
a process indicator enclosed within said chamber formed by said first barrier film;
wherein the combination of said process indicator and said first barrier film are selected to mimic the resistance of a particular product-package combination to a particular sterilization, biological inactivation, or disinfection process, and
wherein said chamber further comprises a front film and a back film, said front film being formed from a material with properties different than a material forming said back film.

2. The process challenge device of claim 1, wherein said first barrier film provides a resistance to a particular sterilization, biological inactivation, or disinfection process greater than or equal to a particular product-package combination.

3. The process challenge device of claim 1, wherein said process indicator comprises an organism selected from the group consisting of:
Bacillus subtilis,
Bacillus stearothermophilus,
Clostridium,
Bacillus circulans,
Bacillus cereus, and
Bacillus Pulmilus.

4. The process challenge device of claim 1, wherein said process indicator comprises a biological enzyme.

5. The process challenge device of claim 1, wherein said process indicator comprises a carrier comprised of a material selected from the group consisting of:
cellulose,
polyester,
ceramic,
plastic,
glass,
fiberglass, and
metal.

6. The process challenge device of claim 1, wherein said barrier film is comprised of a material selected from the group consisting of:
polyolefins,
polyesters,
polybutylene terephthalate,
PETG copolyester,
vinyl-chloride polymers,
polyvinylidene chloride,
polyvinylidene fluoride
polyamides,
ethylene vinyl alcohol,
ethylene vinyl acetate,
aluminized polyester,
silica oxide, and
alumina oxide.

7. The process challenge device of claim 1, wherein said first barrier film is multilayered.

8. The process challenge device of claim 1, further including a second chamber and a separation means between said first chamber and said second chamber.

9. A process challenge device comprising:
a first chamber formed by a first barrier film;
a process indicator enclosed within said first chamber formed by said first barrier film;
a second chamber; and
separation means between said first chamber and said second chamber;
wherein the combination of said process indicator and said first barrier film are selected to mimic the resistance of a particular product-package combination to a particular sterilization, biological inactivation, or disinfection process, and
wherein said second chamber encloses a quantity of a test medium.

10. The process challenge device of claim 9, wherein said test medium is a soybean casine digest medium.

11. The process challenge device of claim 1, further comprising a means for indicating that the device has been exposed to a sterilization, biological inactivation, or disinfection process.

12. A process challenge device comprising:
a first chamber formed by a first barrier film;
a process indicator enclosed within said first chamber formed by said first barrier film;
a second chamber; and
separation means between said first chamber and said second chamber;
wherein the combination of said process indicator and said first barrier film are selected to mimic the resistance of a particular product-package combination to a particular sterilization, biological inactivation, or disinfection process, and
wherein said second chamber is formed from a second barrier film, said second barrier film being formed from a material different than said first barrier film.

13. The process challenge device of claim 12, wherein said second barrier film of said second chamber provides a different resistance to a particular sterilization, biological inactivation, or disinfection process than said first barrier film of said first chamber.

14. A process challenge device comprising:
a first chamber and a second chamber, said first chamber being formed by a first film, said second chamber being formed by a second film;
a process indicator enclosed within said first chamber;
a quantity of a culture medium enclosed within said second chamber; and
a separation means between said first and second chambers.

15. The process challenge device of claim 14, wherein the combination of said process indicator and said first barrier film are selected to mimic the resistance of a particular product-package combination to a particular sterilization, biological inactivation, or disinfection process.

16. The process challenge device of claim 14, wherein said separation means between said first and second chambers is frangible.

17. The process challenge device of claim 14, wherein said separation means between said first and second chambers is removable.

18. The process challenge device of claim 14, wherein said separation means between said first and second chambers is breachable.

19. The process challenge device of claim 14, wherein said first film of said first chamber is formed from a material with properties different than a material forming said second film of said second chamber.

20. The process challenge device of claim 14, wherein said first film provides a different resistance to a sterilization, biological inactivation, or disinfection process than a resistance provided by said second film to said sterilization, biological inactivation, or disinfection process.

21. The process challenge device of claim 14, further comprising means for indicating that the device has been exposed to a sterilization, biological inactivation, or disinfection process.

22. A process challenge device comprising:
   a first chamber formed of a first material;
   a window into said first chamber formed of a second material; and
   a process indicator enclosed within said chamber formed by said first barrier film;
   wherein the combination of said process indicator and said second material are selected to mimic the resistance of a particular product-package combination to a particular sterilization, biological inactivation, or disinfection process.

23. The process challenge device of claim 22, further comprising a second chamber and a separation means between said first chamber and said second chamber.

24. The process challenge device of claim 23, wherein said second chamber encloses a quantity of a test medium.

* * * * *